United States Patent
Motoki (10) Patent No.: US 6,920,465 B2
(45) Date of Patent: Jul. 19, 2005

(54) RADIATION IMAGE RADIOGRAPHING APPARATUS

(75) Inventor: Wataru Motoki, Tokyo (JP)

(73) Assignee: Konica Corporation, Tokyo (JP)

( * ) Notice: Subject to any disclaimer, the term of this patent is extended or adjusted under 35 U.S.C. 154(b) by 373 days.

(21) Appl. No.: 10/192,628

(22) Filed: Jul. 10, 2002

(65) Prior Publication Data

US 2003/0016785 A1 Jan. 23, 2003

(30) Foreign Application Priority Data

Jul. 18, 2001 (JP) .................................. 2001-218123

(51) Int. Cl.[7] ............................................ G06F 17/30
(52) U.S. Cl. ................................................ 707/104.1
(58) Field of Search ...................... 707/1, 104.1; 378/1; 345/10, 23–25; 709/217, 218; 710/5, 20; 714/746

(56) References Cited

U.S. PATENT DOCUMENTS

| | | | | |
|---|---|---|---|---|
| 5,329,445 A | * | 7/1994 | Mukai | 382/128 |
| 5,361,202 A | * | 11/1994 | Doue | 705/3 |
| 5,895,462 A | * | 4/1999 | Toki | 707/3 |
| 6,431,440 B1 | * | 8/2002 | Tsuchino | 235/380 |
| 6,453,059 B2 | * | 9/2002 | Ogawa | 382/132 |
| 6,570,679 B2 | * | 5/2003 | Saruwatari | 358/468 |
| 6,762,429 B2 | * | 7/2004 | Aonuma | 250/583 |

OTHER PUBLICATIONS

Jacky et al., Relational Database: A Radiation Therapy Machine Control Software Development Tool, Engineering in Medicine & Biology Society. Images of the 25th Century. Proceedings of the Annual Inter. Conf. of the IEEE EG, Nov. 1989, p. 1918–1919 vol. 6.*

* cited by examiner

Primary Examiner—Greta Robinson
(74) Attorney, Agent, or Firm—Frishauf, Holtz, Goodman & Chick, P.C.

(57) ABSTRACT

A radiation image radiographing apparatus includes an information input section having an input screen with which a patient information item and a radiographing information item are inputted; a memory section; an image input section to conduct inputting a radiation radiography image; a control section to check whether a predetermined set of patient information items of the patient are inputted in the memory section when the image input section starts inputting a radiation radiography image of the patient. When the predetermined set of patient information items are not inputted in the memory section, the control section prohibits inputting a radiation radiography image of the patient and controls the information input section to indicate an un-inputted patient information item on the input screen in such a way that the un-inputted patient information item is inputted on the input screen.

9 Claims, 7 Drawing Sheets

| MODE·ROUTINE | ID 00001　　NAME KONICA TAROU<br>ENTER PATIENT INFORMATION | CONFIRM | CANCEL |

PATIENT ID　　　　00001
NAME IN ROMAN　　Konica Tarou
NAME IN KANA　　　コニカ　タロウ
NAME IN KANJI　　　コニカ　太郎
SEX　　　　　　　　1234567890123456 ▼
DATE OF BIRTH　　　December 12, 1234
AGE　　　　　　　　123 Years 12 Months Old
PATIENT COMMENT　123456789012345678901234567890 12

SEARCH

PATIENT

| MODE: ROUTINE | ENTER STUDY INFORMATION | | ID 00001 | NAME: KONICA TAROU | | CONFIRM | CANCEL |
|---|---|---|---|---|---|---|---|

| | | |
|---|---|---|
| ACCEPTANCE NO | 12345678901234567 | |
| STUDY ID | 12345678901234567 | |
| ANOTHER STUDY ID | 123456789012 | |
| STUDY PRIORITY | 12345678901234567 ▼ | |
| STUDY COMMENT | 1234567890123456789012345678901234567890123456789012 | |
| PLANNED STUDY DATE | December 12, 1234, 12 12'12" | |
| REASON FOR STUDY | 1234567890:23456789012345678901234567890123456789012 | |
| REQUESTING DOCTOR | 1234567890123456789012345678901234567890123456789012 | |
| REQUESTING DEPARTMENT | 1234567890123456789012345678901234567890123456789012 | |
| STUDY DATE/TIME | December 12, 1234, 12 12'12" | |
| INQUIRING DOCTOR | 1234567890123456789012345678901234567890123456789012 | |
| RECORDING DOCTOR | 1234567890123456789012345678901234567890123456789012 | |
| IMAGE READING DOCTOR | 1234567890123456789012345678901234567890123456789012 | |
| DIAGNOSTIC REMARKS | 1234567890123456789012345678901234567890123456789012 | |
| ATTENDING DOCTOR | 1234567890123456789012345678901234567890123456789012 | |
| RADIOLOGIST | 1234567890123456789012345678901234567890123456789012 | |
| STUDY REGION | 12345678901234567 ▼ | |
| VIEWING POSITION | 12345678901234567 ▼ | |
| SERIES NO | 123456789012 | |
| IMAGE PROPERTY | 12345678901234567 ▼ | |

| STUDY | IMAGE |
|---|---|

FIG. 5

MODE: ROUTINE | ENTER STUDY INFORMATION

ID 00001     NAME: KONICA TAROU

| Field | Value | Unit |
|---|---|---|
| IMAGING DATE/TIME | December 12, 1234, 12 12'12" | |
| IMAGE NO | 123456789012 | |
| DIRECTION OF PATIENT | 123456789012 ▼ | |
| IMAGE COMMENT | 1234567890123456789012 | |
| QUALITY CONTROL IMAGE | 123456789012 ▼ | |
| KVP | 1234567890123456 | KVP |
| EXPOSURE TIME | 123456789012 | msec |
| X-RAY TUBE CURRENT | 123456789012 | mA |
| EXPOSURE RATE | 123456789012 | mAs |
| FOCUS | 1234567890123456 | mm |
| SOURCE-DETECTOR | 1234567890123456 | mm |
| SOURCE-PATIENT | 1234567890123456 | mm |
| RECTIFICATION TYPE | 123456789012 ▼ | |
| ANODE TARGET MATERIAL | 123456789012 ▼ | |
| EXPOSURE CONTROL MODE | 123456789012 ▼ | |

| Field | Value | Unit |
|---|---|---|
| CONTRAST MEDIUM | 1234567890123456789012 | |
| CONTRAST MEDIUM PATH | 1234567890123456789012 | |
| VOLUME OF CONTRAST MEDIUM | 12345678901234556 | ml |
| STARTING TIME | 12:12'12" | |
| STOPPING TIME | 12.12'12" | |
| OVERALL DOSAGE | 1234567890123456 | ml |
| CONTRAST MEDIUM FLOW RATE | 1234567890123456 | ml / sec |
| FLOW DURATION | 1234567890123456 | sec |
| CONTRAST MEDIUM COMPOSITION | 1234567890123456 ▼ | |
| COMPOSITION CONCENTRATION | 1234567890123456 | mg |

23a     CONFIRM   CANCEL

STUDY    IMAGE

FIG. 6

| MODE ROUTINE | ENTER INFORMATION ON PATIENT AND STUDY | | CONFIRM | CANCEL |

| | | | |
|---|---|---|---|
| PATIENT ID | 1234567890 | PLANNED STUDY DATE | December 12, 1234, 12:12'12" |
| NAME IN ROMAN | | REASON FOR STUDY | 12345678901234567890123456789012 |
| NAME IN KANA | | REQUESTING DOCTOR | 12345678901234567890123456789012 |
| NAME IN KANJI | | REQUESTING DEPARTMENT | 12345678901234567890123456789012 |
| SEX | 12345678901234 56 ▼ | STUDY DATE/TIME | December 12, 1234, 12:12'12" |
| DATE OF BIRTH | December 12, 1234 | INQUIRING DOCTOR | 12345678901234567890123456789012 |
| AGE | 123 Years 12 Months Old | RECORDING DOCTOR | 12345678901234567890123456789012 |
| PATIENT COMMENT | 12345678901234567890123456789012 | IMAGE READING DOCTOR | 12345678901234567890123456789012 |
| | | DIAGNOSTIC REMARKS | 12345678901234567890123456789012 |
| | | ATTENDING DOCTOR | 12345678901234567890123456789012 |
| | | RADIOLOGIST | 12345678901234567890123456789012 |
| | | STUDY REGION | 12345678901234 56 ▼ |
| | | VIEWING POSITION | 1234567890123456 ▼ |
| | | SERIES NO | 123456789012 |
| | | IMAGE PROPERTY | 1234567890123456 ▼ |

24a — patient section
24b — study section
24 — overall window

SEARCH    PATIENT

FIG. 7
PRIOR ART

RADIATION IMAGE RADIOGRAPHING APPARATUS

BACKGROUND OF THE INVENTION

The present invention relates to a radiation image radiographing apparatus to indicate a screen on which plural items to determine information necessary for radiographing a radiation image are inputted.

Figure 7:
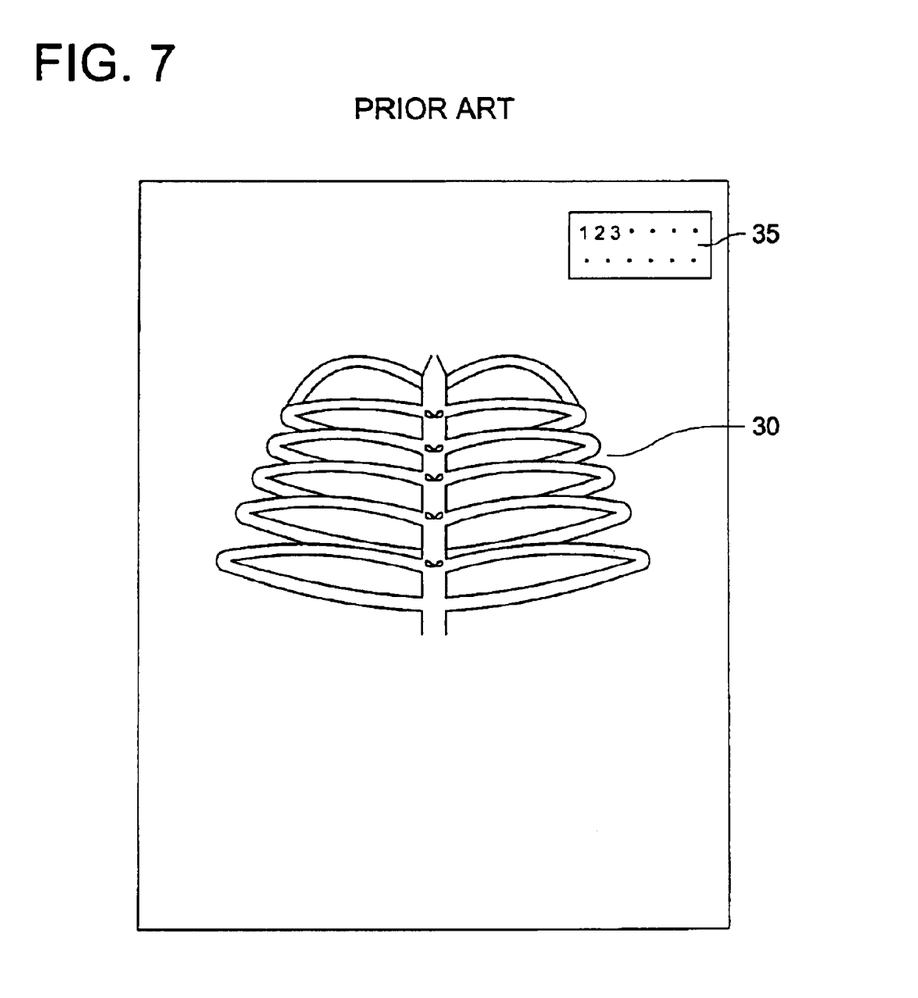
FIG. 7 is a view showing an example of a diagnostic image.

Patient ID information (ID number, patient name, and others) and order information (the region to be radiographed, the radiographing direction for radiography, and others) are required for radiography with a radiation image radiographing apparatus, and before radiation imaging takes place, the ID information and the order information are entered into the radiation image radiographing apparatus. As shown in the diagnostic image of FIG. 7, patient ID information 35, along with the medical image 30 of the patient, is displayed as a character image, and diagnostic results based on this medical image are recorded on charts of the patient specified by the patient ID number. Since the patient information including the patient ID number is important information linking the medical image and the patient in this way, it is not permitted to add or modify patient information after radiography was completed. It is therefore important to accurately enter all the patient information required for radiation imaging. Also, for the conventional radiation image radiographing apparatus as set forth above, since the ID information and the order information are displayed in independent screen modes, the operator must perform operations such as screen display development operations. It is therefore necessary for the operator to perform various operations when entering the information required for radiography.

SUMMARY OF THE INVENTION

The object of the present invention, with the above-described situation in view, is to provide a radiation image radiographing apparatus that enables accurate entry of all the information required for radiation imaging.

(1) A radiation image radiographing apparatus for radiographing a patient, comprises:

an information input section having an input screen with which a patient information item and a radiographing information item are inputted;

a memory section to memorize the patient information item and the radiographing information item;

an image input section to conduct inputting a radiation radiography image;

a control section to check whether a predetermined set of patient information items of the patient are inputted in the memory section when the image input section starts inputting a radiation radiography image of the patient;

wherein when the predetermined set of patient information items are not inputted in the memory section, the control section prohibits inputting a radiation radiography image of the patient and controls the information input section to indicate an un-inputted patient information item on the input screen in such a way that the un-inputted patient information item is inputted on the input screen.

(1-1) In order to fulfill the above object, a first radiation image radiographing apparatus based on the present invention is characterized in that said apparatus is equipped with an input section which has an input screen for entering patient information and radiographic information, a memory section for storage of the patient information and radiographic information that have been entered, an execution data input section for executing radiation imaging, and a control section for confirming whether the required patient information is already stored within said memory section when radiation imaging data is entered from said execution data input section, and in that if the required patient information is not yet stored within the memory section, said control section will prohibit the execution of radiation imaging and display data-missing patient information items in the input screen mode of the input section.

(1-2) The required patient information mentioned above refers to at least one of the ID code, name, the date of berth, sex of the patient and a radiologist.

(1-3) If a plurality of un-inputted items (data-missing input items) are present as the required patient information mentioned above, these items will be displayed one by one.

(1-4) When the required patient information is already stored within the memory section, the control section will release the prohibited status of the execution of radiation imaging.

The above-described construction based on the present invention enables accurate and reliable entry of all the information required for radiation imaging.

(2) In order to fulfill the above object, a second radiation image radiographing apparatus based on the present invention provides a screen mode for entering a plurality of input items during entry of the information required for radiation imaging, wherein said radiation image radiographing apparatus is characterized in that it is constructed so that input screen modes for any un-inputted items present in the aforementioned screen mode are sequentially displayed for each item so as to enable entry into the items corresponding to the aforementioned input screen mode which has been displayed.

In such radiation image radiographing apparatus as outlined above, input screen modes on un-inputted items are sequentially displayed for each item and these screen modes are not displayed for the items that do not require data entry. Operator actions are reduced since the operator only needs to enter data into the necessary items of the input screen modes sequentially displayed. In this case, since the display items and the order of display can be arbitrarily specified, data entry into the necessary items only is possible and these items can be displayed in the order that the operator is usually to use, with the result that ease in operations is increased.

(3) Also, a third radiation image radiographing apparatus based on the present invention provides a plurality of screen modes for entering a plurality of input items during entry of the information required for radiation imaging, wherein said radiation image radiographing apparatus is characterized in that it is constructed so that when the aforementioned screen modes contains un-inputted items, these screen modes will be sequentially displayed so as to enable data to be entered into the un-inputted items contained in the particular screen mode.

In such radiation image radiographing apparatus as outlined above, screen operations are reduced since the screen modes that contain un-inputted items are sequentially displayed and since data can be entered into the un-inputted items. In this case, since the display items and the order of display can be arbitrarily specified, data entry into the necessary items only is possible and a plurality of screen modes can be displayed according to the particular work flow, with the result that ease in operations is increased.

Also, a fourth radiation image radiographing apparatus based on the present invention provides a screen mode for entering a plurality of input items during entry of the information required for radiation imaging, wherein said radiation image radiographing apparatus is characterized in that it is constructed so that the above-mentioned items required for radiation imaging can be selected and so that the input screen modes relating to the selected items are integratedly displayed in one screen mode so as to enable data on those items to be entered in a single screen mode.

In such radiation image radiographing apparatus as outlined above, since the screen mode can be customized and since the input screen modes relating to the items required for radiography are integratedly displayed in one screen mode so as to enable data on those items to be entered in a single screen mode, screen operations are reduced and ease in the operations is increased.

Also, as with the first and second radiation image radiographing apparatus, the third and fourth radiation image radiographing apparatus can be constructed so that when un-inputted items are included in the particular screen mode, input screen modes relating to these un-inputted items can be sequentially displayed item by item so as to enable data to be entered into the items corresponding to the displayed input screen mode. Hereby, screen operations are reduced and ease in the operations improves.

BRIEF DESCRIPTION OF THE DRAWINGS

FIG. 3 is a view showing examples of the input screen modes displayed when un-inputted items exist in the screen mode of FIG. 2, wherein FIG. 3(a) shows the screen mode for entering the sex of the patient and FIG. 3(b) shows the screen mode for entering the date of birth of the patient.

FIG. 5 is a view showing an example of another screen mode displayed on the display portion of the controller so as to enable entry of study information for radiation imaging with the radiation image radiographing apparatus of FIG. 1.

DETAILED DESCRIPTION OF THE PREFERRED EMBODIMENT

The preferred embodiment of the present invention is described in detail below using drawings.

Figure 1:
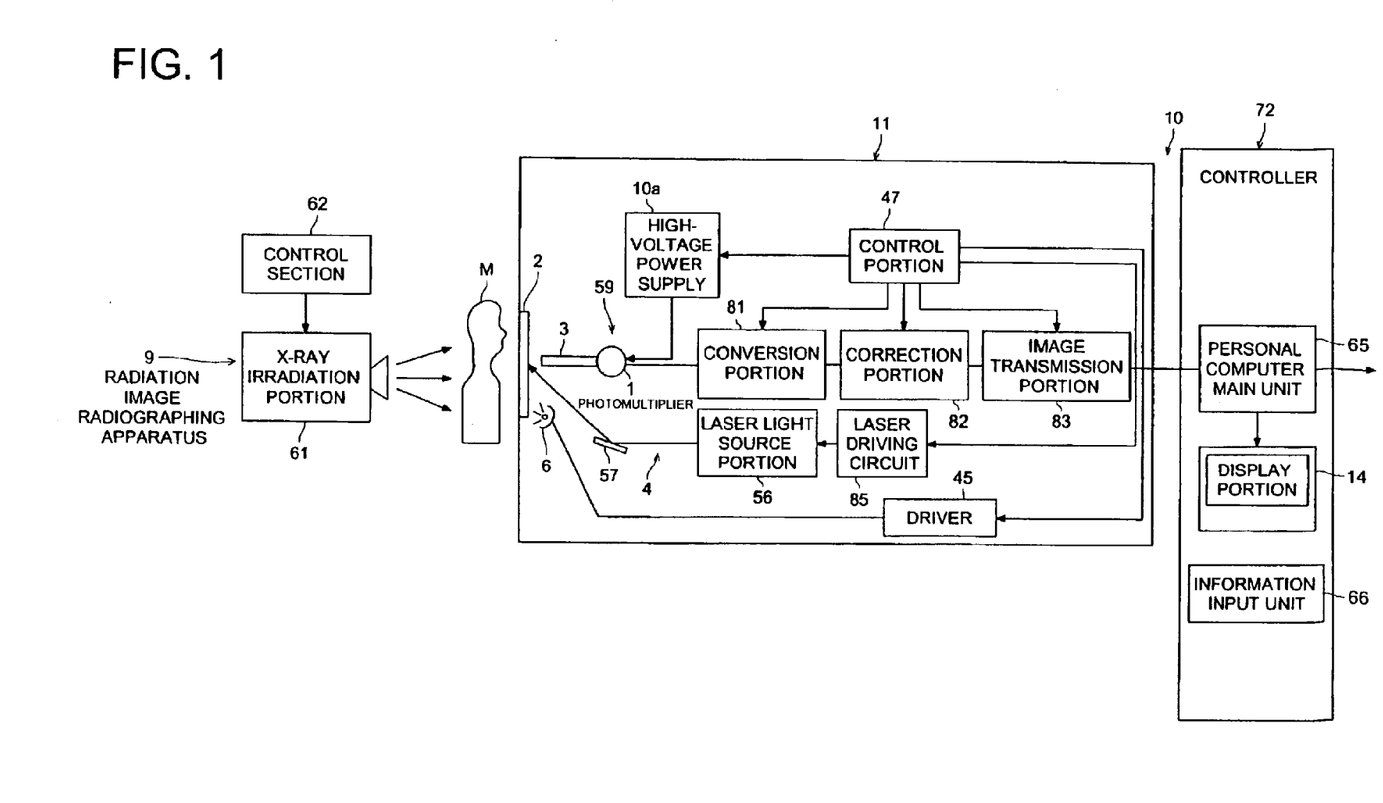
FIG. 1 is a block diagram showing the entire major section of the radiation image radiographing apparatus in the preferred embodiment of the present invention.
Figure 2:
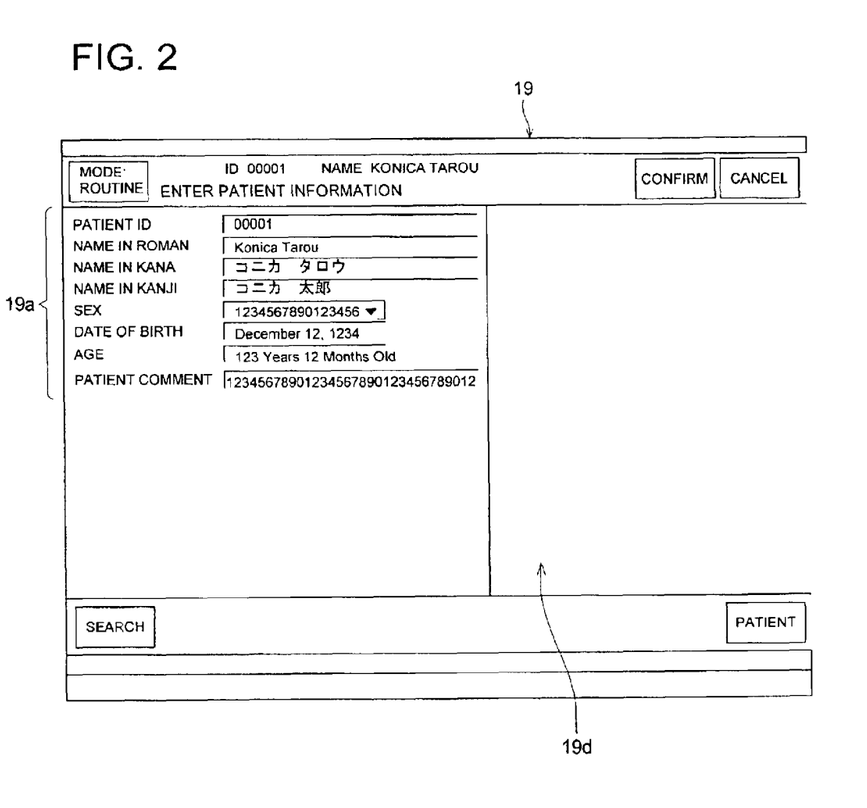
FIG. 2 is a view showing an example of the patient information input screen mode displayed on the display portion of the controller shown in FIG. 1.
Figure 3:
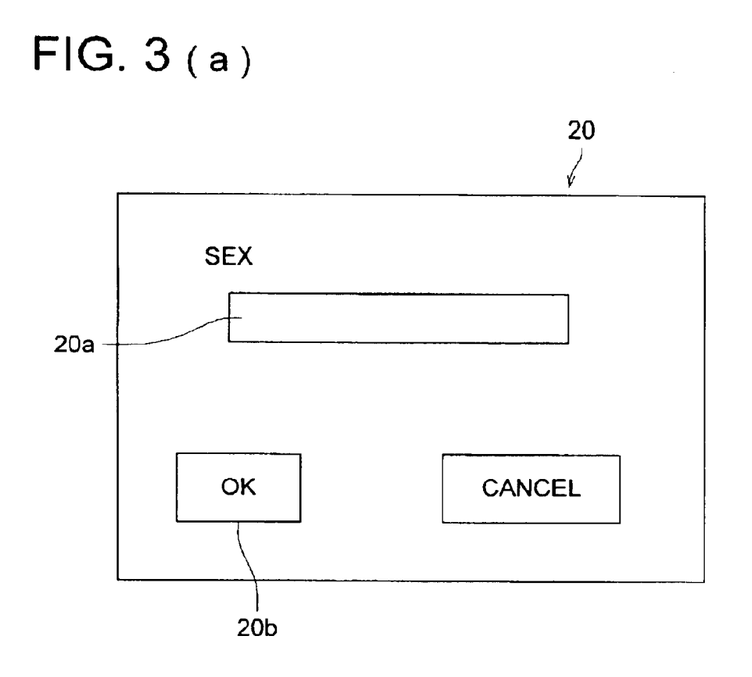

FIG. 1 is a block diagram showing the entire major section of the radiation image radiographing apparatus in the preferred embodiment of the present invention, FIG. 2 is a view showing an example of the patient information input screen mode displayed on the display portion of the controller shown in FIG. 1, and FIG. 3 is a view showing examples of the input screen modes displayed when un-inputted items exist in the screen mode of FIG. 2.

As shown in FIG. 1, radiation image radiographing apparatus 10 has a reader 11 for reading the radiation images that have been recorded by the radiation image radiographing apparatus, and a controller 72 for controlling the reader 11. Reader 11 is constructed so that by use of photo-stimulated phosphors which, after the emission of radiation has resulted in part of the radiation energy being stored and then visible light or laser light or other stimulated light has been emitted, will exhibit photo-stimulated luminescence according to the stored radiation energy, the radiation image information of a subject (patient) M that has been obtained by irradiating X-rays from an X-ray irradiation portion 61 (controlled by the control section 62 of the radiation image radiographing apparatus 9) to the body of the subject is temporarily stored onto a photo-stimulated phosphor sheet 2 having storable phosphors on its substrate, then laser light scanning from a scanning optical portion 4 activates the photo-stimulated phosphors sequentially to exhibit photo-stimulated luminescence, and the light by the photo-stimulated luminescence is photoelectrically read using a photomultiplier 1 to obtain an image signal. Reader 11 emits erasable light from a halogen lamp 6 to the photo-stimulated phosphor sheet 2 existing after the image signal has been read, and then releases the radiation energy remaining on this sheet to prepare for the next radiography.

Reader 11 comprises a photo-stimulated phosphor sheet 2 for accepting the radiation image information of the subject, a laser light source portion 56 consisting of the laser diodes and other elements that emits laser light as stimulated light to the photo-stimulated phosphor sheet 2, a laser driving circuit 85 for driving the laser light source portion 56, an optical system 57 for scanning the photo-stimulated phosphor sheet 2 by use of the laser light from the laser light source portion 56, and a light-condensing/reading portion 59 for condensing photo-stimulated luminescent light (the light obtained as a result of the excitation of stimulating laser light) and photoelectrically converting the light to obtain an image signal. The light-condensing/reading portion 59 has a light guide 3 for condensing the laser-stimulated luminescent light, a photomultiplier 1 for photoelectrically converting the condensed light by use of the light guide 3, a high-voltage power supply 10a for applying a voltage to the photomultiplier 1, a conversion portion 81 by which the current signal from the photomultiplier 1 is converted into a digital signal by current-voltage conversion, voltage amplification, A-D conversion, or the like, a correction portion for correcting the digital signal that has been obtained from the conversion process of the conversion portion 81, and an image transmission portion 83 by which the digital signal that has been corrected by the correction portion 82 is transmitted. The digital signal of the radiation image information which has been read is transmitted to a controller 72. The correction portion 82 is made of a RISC processor and corrects a response delay in the digital signal and/or the nonuniformity thereof.

In order to release the radiation energy remaining on the photo-stimulated phosphor sheet 2 existing after the image signal has been read, reader 11 further has a halogen lamp 6 for emitting erasable light, and a driver 45 for driving the halogen lamp 6. Reader 11 also has a control section 47 that controls the laser driving circuit 5, the high-voltage power supply 10a, the conversion portion 81, the correction portion 82, the image transmission portion 83, and the driver 45. In addition, the scanning optical portion 4 (this includes the laser light source portion 56 and optical system 57 of the reader 11), the light guide 3, the photomultiplier 1, and the halogen lamp 6 integrally move as a sub-scanning unit (not shown in the figure) in a sub-scanning direction vertical to the laser scanning direction, by the action of a ball screw mechanism. The sub-scanning unit sub-scans by moving when an image is read, and erases the after-image by activating the halogen lamp while reciprocating.

Controller 72 is equipped with a personal computer main unit 65, which constitutes the image processing portion and other elements and contains memories such as a hard disk and RAM, with an information input unit 66 including a mouse and a keyboard, and with a display portion 14. In controller 72, the digital signal of the radiation image information which has been received from reader 11 is temporarily stored into a memory, then after the signal has undergone image processing and display on display portion 14 and image processing have been controlled according to the input operations from information input unit 66, the image-processed radiation image information is output. Also, a screen mode for entering the information required for radiation imaging is displayed on display portion 14 by the control of the controller 72.

Next, screen modes for entering data into each item in order to set the information required for radiography with the radiation image radiographing apparatus of FIG. 1 are described below.

For radiography with the radiation image radiographing apparatus of FIG. 1, as shown in FIG. 2, a screen mode 19 for entering patient information is displayed on the display portion 14 of the controller 72. Screen mode 19 is displayed so that data can be entered into a plurality of items, such as the ID, name, sex, and date of birth of the patient, as the patient information required for radiography. In this case, when radiography with the radiation image radiographing apparatus of FIG. 1 is started, if the controller 2 judges that there are any un-inputted items relating to the patient information required for the radiography, the radiography itself will be prohibited and those un-inputted items will be displayed on the display portion.

If, in the screen mode 19 of FIG. 2, the patient ID and the patient name are entered and sex information 19b and date-of-birth information 19c are not entered, controller 72 will provide control so that such sex information input screen mode 20 as shown in FIG. 3(a) will be displayed on the display portion 14 of the controller 72. When sex is entered in the input field 20a of the input screen mode 20 and then an OK button 20b is pressed, such date-of-birth information input screen mode 21 as shown in FIG. 3(b) will be displayed on display portion 14. In the input screen mode 21, the date of birth is entered in an input field 20a and then an OK button 21b is pressed. Hereby, entry into the un-inputted items is completed and the entered information is displayed in the sex input field 19b and date-of-birth input field 19c of the screen mode 19 shown in FIG. 2. And the thus-entered patient information is registered in the radiation image radiographing apparatus of FIG. 1.

In this way, when un-inputted items 19b and 19c exist in the screen mode 19 of FIG. 2, input screen modes 20 and 21 are sequentially displayed for each item and the operator only needs to enter data into the necessary items of the input screen modes sequentially displayed. Thus, screen operations are reduced. Also, since only the items that require data entry are displayed, the operating procedure relating to entry is readily understandable and the operations themselves are simplified. The display items in FIG. 2 and the order of input screen mode display can be arbitrarily specified. In addition, such input screen modes 20 and 21 as shown in FIG. 3 can be displayed in overlapped form on the area 19d of FIG. 2.

In this manner, when all the information required for radiography is entered, controller 2 will release the prohibited status of radiation imaging to enable the radiation imaging operation of the radiation image radiographing apparatus.

Figure 4:
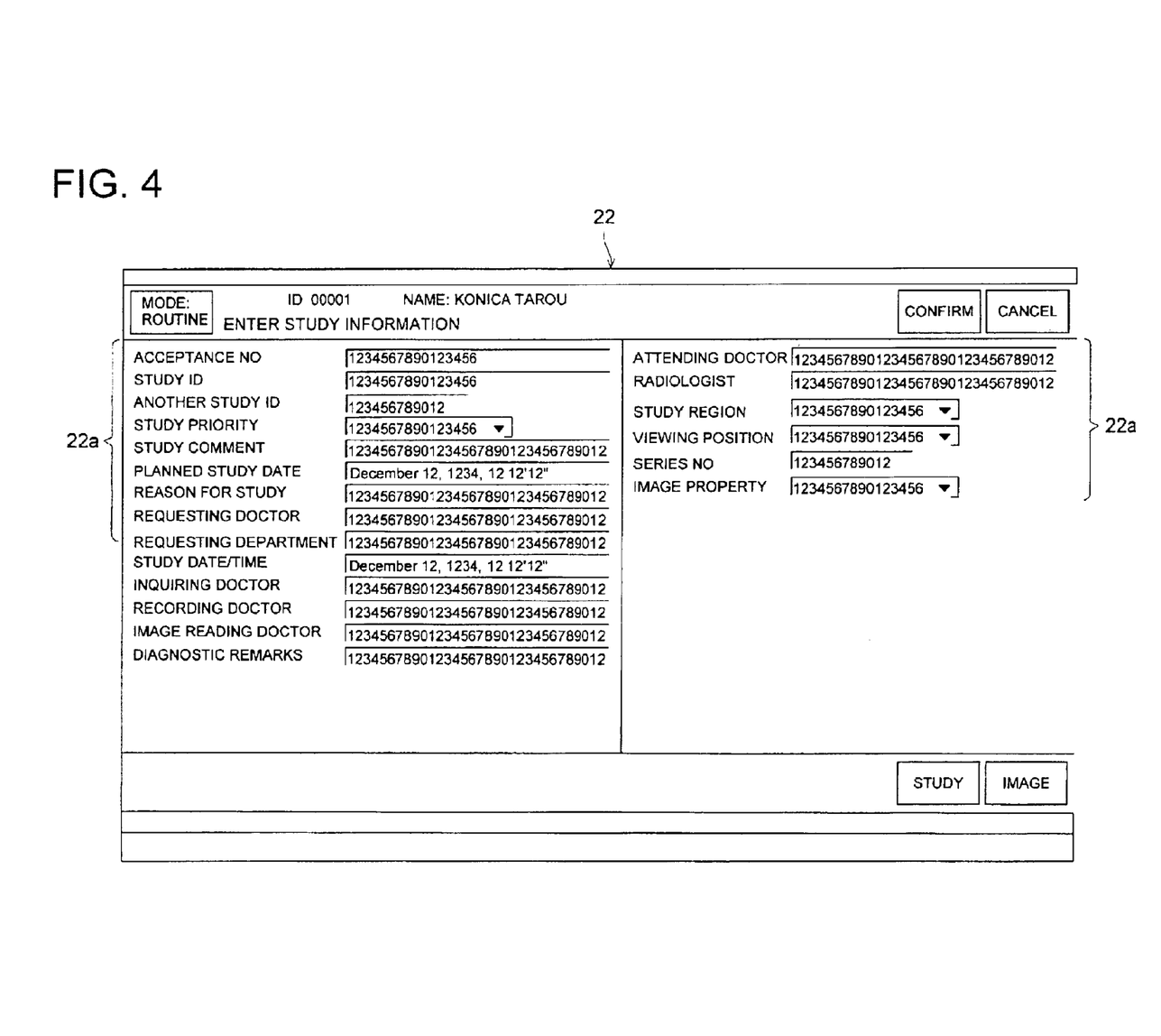
FIG. 4 is a view showing an example of a screen mode displayed on the display portion of the controller so as to enable entry of study information for radiation imaging with the radiation image radiographing apparatus of FIG. 1.

Next, other screen modes are described below using FIGS. 4 and 5. FIGS. 4 and 5 are views showing the screen modes 22 and 23, respectively, that are displayed on display portion 14 in order to enable entry of the study information required for radiography with the radiation image radiographing apparatus of FIG. 1. A plurality of input fields 22a and 23a on study information are displayed in screen modes 22 and 23. In this case, if any un-inputted items are present in a plurality of screen modes 22 and 23 (including the above-described patient information input screen mode 19 of FIG. 3), these screen modes will be displayed in order.

Because of the construction described above, for example, if any un-inputted items are present in the fields 22a and 23a of the screen modes 22 and 23, control by controller 72 will first display screen mode 22 to enable data entry into the corresponding un-inputted items, and then display screen mode 23 to enable data entry into the corresponding un-inputted items. Thus, screen operations can be reduced. It also becomes possible to arbitrarily specify the order of screen mode display and to display screen modes in the order matching the work flow, and increases the ease of operations. In addition, screen modes 19, 22, and 23 can be so configured as to be split into even more screen modes, in which case, screen modes with any un-inputted items can also be displayed in order.

Figure 6:
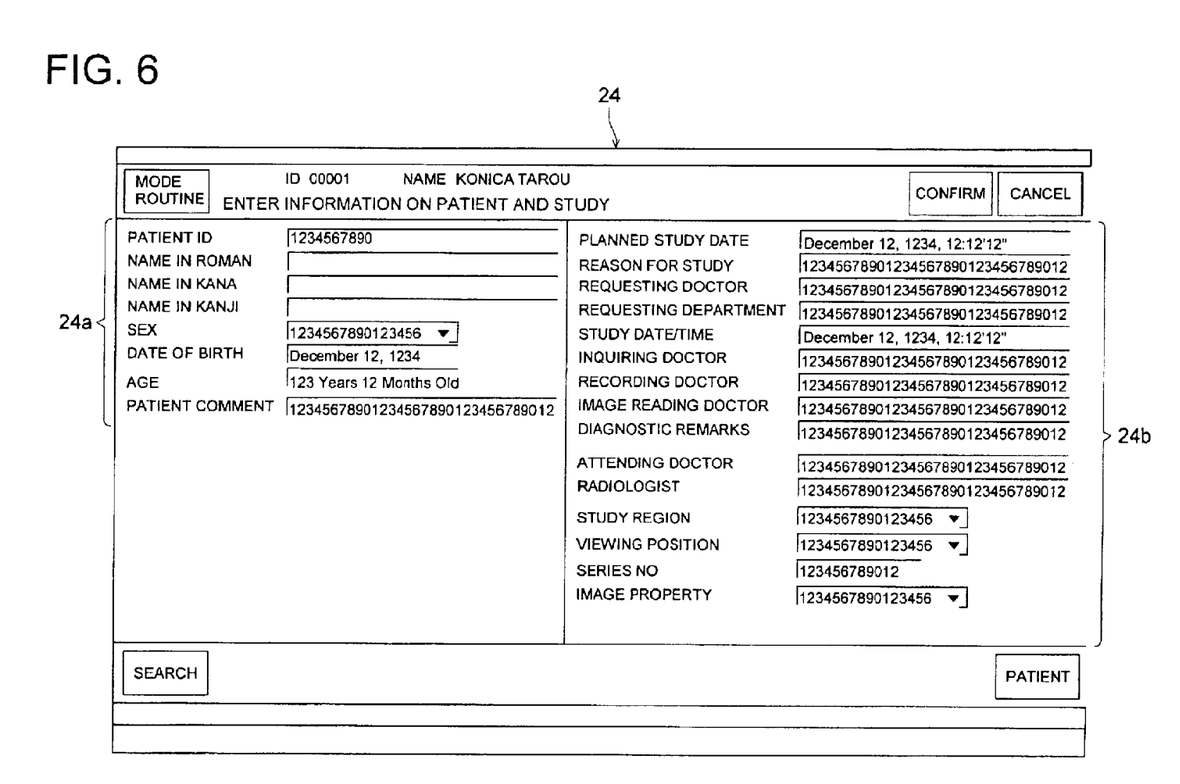
FIG. 6 is a view showing an example of a screen mode displayed on the display portion of the controller so as to enable entry of patient information and study information for radiation imaging with the radiation image radiographing apparatus of FIG. 1.

Next, yet another screen mode is described below using FIG. 6. FIG. 6 is a view showing the screen mode 24 displayed on display portion 14 in order to enable entry of the patient information and study information required for radiography with the radiation image radiographing apparatus of FIG. 1. A plurality of input fields 24a on patient information and a plurality of input fields 24b on study information are displayed in the screen mode 24 of FIG. 6. Each item in these fields 24a and 24b can be arbitrarily selected in other screen modes.

In the screen mode 24 of FIG. 6, since the patient information and study information required for radiation imaging can be entered in a single screen mode, the necessary item entry operations in one screen mode are possible and this reduces screen operations and increases the ease of operations.

Although the preferred embodiment of the present invention has been described above, this embodiment does not limit the invention and can take various modes of modification within the scope of the technical philosophy of the invention. The screen modes of FIGS. 2 to 6, for example, are examples and these screen modes can, of course, be displayed in other formats. In FIGS. 2 and 3, screen modes concerning patient information are described. When such study information as shown in FIGS. 4 and 5 is to be entered, input screen modes similar to those of FIGS. 2 and 3 can also be sequentially displayed for each item so as to enable entry into un-inputted items. In addition, when the screen modes that include un-inputted items, such as FIGS. 4, 5, and 6, are to be displayed, such input screen modes as shown in FIG. 3 can be sequentially displayed for each item so as to enable entry into un-inputted items.

According to the present invention, it is possible to provide a radiation image radiographing apparatus that can reduce the operations of the operator when the data is to be entered into the plurality of items required for radiation imaging.

What is claimed is:

1. A radiation image radiographing apparatus for radiographing a patient, comprising:

an information input section having an input device to input data and an input screen on which a plurality of predetermined patient information items are indicated on a first input screen mode so that data of the plurality of predetermined patient information items are input by the input device while viewing the input screen;

a memory section which stores the input data of the plurality of predetermined patient information items;

an image input section to input a radiation radiography image; and a control section which checks whether all of the data of the plurality of predetermined patient information items of the patient are input in the memory section when the image input section begins to input a radiation radiography image of the patient;

wherein if any data of the plurality of predetermined patient information items of the patient is not input in the memory section, the control section prohibits input of a radiation radiography image of the patient and controls the information input section to indicate only the patient information item which was not input on a second input screen mode different from the first input screen mode.

2. The radiation image radiographing apparatus of claim 1, wherein when the control section once prohibited inputting a radiation radiography image of the patient, the control section releases the prohibition to conduct inputting a radiation radiography image of the patient after the control section confirmed that the predetermined set of patient information items are inputted in the memory section.

3. The radiation image radiographing apparatus of claim 1 wherein the predetermined set of patient information items include a patient ID code and at least one of a name, sex and date of birth.

4. The radiation image radiographing apparatus of claim 1, wherein when plural patient information items are not inputted, the un-inputted plural patient information items are indicated simultaneously on the same screen of the input screen on the second input screen mode.

5. The radiation image radiographing apparatus of claim 1, wherein when a name of a radiologist to conduct inputting a radiation radiography image of the patient is not memorized in the memory section, the control section prohibits the radiographing and controls the input section to indicate an item of the name of a radiologist as an un-inputted item on the input screen.

6. The radiation image radiographing apparatus of claim 1, wherein when plural radiographing information items are to be inputted, the plural radiographing information items are indicated on the input screen on the first input screen mode so that data of the plural radiographing information items are inputted by the input device while viewing the input screen.

7. The radiation image radiographing apparatus of claim 1, wherein when data of plural items among the plurality of predetermined patient information items are not input, the plural items are indicated sequentially on the input screen on the second input screen mode.

8. The radiation image radiographing apparatus of claim 7, wherein the second input screen mode for the un-inputted plural patient information items and the indication sequence order are changeable.

9. The radiation image radiographing apparatus of claim 1, wherein when data of plural items among the plurality of predetermined patient information items are not input, one of the plural items is indicated on the input screen on the second input screen mode and a next one of the plural items is indicated on the input screen after a previous one of the plural items has been input by the input device.

* * * * *